United States Patent
Farag et al.

(10) Patent No.: US 10,242,488 B1
(45) Date of Patent: Mar. 26, 2019

(54) ONE-SIDED TRANSPARENCY: A NOVEL VISUALIZATION FOR TUBULAR OBJECTS

(71) Applicants: Aly Farag, Louisville, KY (US);
Robert Curtin, Columbus, IN (US);
Salwa Elshazly, Louisville, KY (US)

(72) Inventors: Aly Farag, Louisville, KY (US);
Robert Curtin, Columbus, IN (US);
Salwa Elshazly, Louisville, KY (US)

(73) Assignee: Kentucky Imaging Technologies, LLC, Louisville, KY (US)

( * ) Notice: Subject to any disclaimer, the term of this patent is extended or adjusted under 35 U.S.C. 154(b) by 75 days.

(21) Appl. No.: 15/057,683

(22) Filed: Mar. 1, 2016

Related U.S. Application Data

(60) Provisional application No. 62/126,838, filed on Mar. 2, 2015.

(51) Int. Cl.
*G06T 15/08* (2011.01)
*H04N 13/117* (2018.01)
*H04N 13/282* (2018.01)

(52) U.S. Cl.
CPC .......... *G06T 15/08* (2013.01); *H04N 13/117* (2018.05); *H04N 13/282* (2018.05); *G06T 2207/30028* (2013.01); *G06T 2207/30172* (2013.01); *G06T 2210/41* (2013.01)

(58) Field of Classification Search
CPC .......... H04N 13/0014; H04N 13/0011; H04N 13/0282; H04N 13/0278; G06T 15/08; G06T 2210/41; G06T 2207/30172; G06T 2207/30028; G06T 19/003; G06T 2207/10081; A61B 5/4255
See application file for complete search history.

(56) References Cited

U.S. PATENT DOCUMENTS

| | | | | |
|---|---|---|---|---|
| 6,331,116 B1* | 12/2001 | Kaufman | ............... | G06K 9/209 345/418 |
| 6,343,936 B1* | 2/2002 | Kaufman | ............... | G06K 9/209 128/920 |
| 6,909,913 B2* | 6/2005 | Vining | ............... | G06T 7/0012 128/920 |
| 6,928,314 B1* | 8/2005 | Johnson | ............... | G06T 15/08 128/920 |
| 7,194,117 B2* | 3/2007 | Kaufman | ............... | A61B 5/055 378/41 |
| 7,256,780 B2* | 8/2007 | Williams | ............... | G06T 15/08 345/424 |
| 7,304,644 B2* | 12/2007 | Geiger | ............... | G06T 7/0012 345/424 |

(Continued)

OTHER PUBLICATIONS

Curtin et al., One-Sided Transparency: A Novel Visualization for Tubular Objects, 2014 IEEE International conference on Image Processing (ICIP), Conference Oct. 27-30, 2014; Published on-line Jan. 29, 2015.

*Primary Examiner* — John Villecco
(74) *Attorney, Agent, or Firm* — Law Office of J. L. Simunic; Joan L. Simunic

(57) ABSTRACT

The present invention is a unique method for tubular object visualization. The method involves rendering the exterior of the tube invisible while keeping the interior visible. This "One-sided-transparency" technique renders a more complete view of the tube's interior. When applied to virtual colonoscopy (VC), it compares favorably to existing methods.

4 Claims, 2 Drawing Sheets

(56) References Cited

U.S. PATENT DOCUMENTS

| | | | | |
|---|---|---|---|---|
| 7,324,104 B1* | 1/2008 | Bitter | | G06T 7/60 |
| | | | | 345/419 |
| 7,711,163 B2* | 5/2010 | Geiger | | A61B 5/4255 |
| | | | | 382/128 |
| 7,839,402 B2* | 11/2010 | Dekel | | G06T 15/08 |
| | | | | 345/419 |
| 7,853,310 B2* | 12/2010 | Vining | | A61L 35/1076 |
| | | | | 382/128 |
| 7,890,155 B2* | 2/2011 | Burns | | G06T 19/00 |
| | | | | 600/407 |
| 7,924,279 B2* | 4/2011 | Gerritsen | | G06T 15/08 |
| | | | | 345/424 |
| 7,961,187 B2* | 6/2011 | Borland | | G06T 15/06 |
| | | | | 345/419 |
| 8,014,561 B2 | 9/2011 | Farag et al. | | |
| 8,041,141 B2 | 10/2011 | Farag et al. | | |
| 8,073,226 B2 | 12/2011 | Farag et al. | | |
| 8,150,111 B2* | 4/2012 | Borland | | G06T 15/08 |
| | | | | 382/128 |
| 8,259,108 B2* | 9/2012 | Suhling | | A61B 6/032 |
| | | | | 345/419 |
| 9,501,709 B2* | 11/2016 | Ikeda | | G06K 9/46 |
| 9,659,405 B2* | 5/2017 | Wahrenberg | | G06T 15/506 |
| 2002/0113787 A1* | 8/2002 | Ray | | G06T 15/08 |
| | | | | 345/424 |
| 2005/0152588 A1* | 7/2005 | Yoshida | | G06T 7/0012 |
| | | | | 382/128 |
| 2005/0245803 A1* | 11/2005 | Glenn, Jr. | | A61B 5/4255 |
| | | | | 600/407 |
| 2006/0171585 A1* | 8/2006 | Rinck | | A61B 6/504 |
| | | | | 382/173 |
| 2006/0279568 A1* | 12/2006 | Matsumoto | | G06T 19/00 |
| | | | | 345/419 |
| 2007/0003131 A1* | 1/2007 | Kaufman | | G06T 15/08 |
| | | | | 382/154 |
| 2007/0052724 A1* | 3/2007 | Graham | | G06T 19/003 |
| | | | | 345/620 |
| 2007/0071297 A1* | 3/2007 | Geiger | | A61B 5/4255 |
| | | | | 382/128 |
| 2007/0103464 A1* | 5/2007 | Kaufman | | G06T 7/0012 |
| | | | | 345/424 |
| 2008/0297509 A1* | 12/2008 | Matsumoto | | G06T 15/08 |
| | | | | 345/424 |
| 2009/0010507 A1* | 1/2009 | Geng | | G06T 7/593 |
| | | | | 382/128 |
| 2009/0016589 A1* | 1/2009 | Wolf | | G06T 7/0012 |
| | | | | 382/131 |
| 2009/0225077 A1* | 9/2009 | Sudarsky | | G06T 7/60 |
| | | | | 345/423 |
| 2011/0026793 A1* | 2/2011 | Goel | | G06T 7/60 |
| | | | | 382/131 |
| 2011/0063288 A1* | 3/2011 | Valadez | | G06T 15/08 |
| | | | | 345/419 |
| 2013/0223702 A1* | 8/2013 | Holsing | | A61B 5/113 |
| | | | | 382/128 |
| 2014/0146044 A1* | 5/2014 | Cvetko | | G06T 19/003 |
| | | | | 345/420 |
| 2016/0371883 A1* | 12/2016 | Merkine | | A61B 1/2676 |
| 2018/0308278 A1* | 10/2018 | Qiu | | G06T 15/506 |

* cited by examiner a. Fully visible polyp b. Partially visible polyp c. Fully transparant polyp

ONE-SIDED TRANSPARENCY: A NOVEL VISUALIZATION FOR TUBULAR OBJECTS IN THE UNITED STATES PATENT AND
TRADEMARK OFFICE NON-PROVISIONAL
UTILITY PATENT APPLICATION FOR
ONE-SIDED TRANSPARENCY: A NOVEL
VISUALIZATION FOR TUBULAR OBJECTS Total Drawing Sheets: 2

Suggested Figure for Publication: 5

Micro Entity Status is Claimed.
Domestic Benefit Information: The present application claims priority to U.S. Patent Application 62/126,838 filed 2015 Mar. 2, currently pending, which is incorporated by reference in its entirety.
No claim to foreign priority.
DO NOT PUBLISH: I hereby request that the attached application not be published under 35 U.S.C. 122(b) and certify that the invention disclosed in the attached application has not and will not be the subject of an application filed in another country, or under a multilateral international agreement, that requires publication at eighteen months after filing.
Inventor Information:
  Aly Farag of Louisville, Ky., a citizen of the United States of America
  Robert Curtin of Columbus, Ind., a citizen of the United States of America
  Salwa Elshazly of Louisville, Ky., a citizen of the United States of America
  The inventors named above may be reached by mail at Kentucky Imaging Technologies, 1703 Golden Leaf Way, Louisville, Ky. 40245.
Correspondence and Representative Information:
  Joan Simunic, Registration 43125, Customer Number 53779
  Attorney Docket KIT1501NPA

CROSS-REFERENCE TO PRIOR APPLICATIONS

The present application claims priority to U.S. Patent Application 62/126,838 filed 2015 Mar. 2, currently pending, which is incorporated by reference in its entirety.

FIELD OF THE INVENTION

The present invention is a unique method for tubular object visualization. The method involves rendering the exterior of the tube invisible while keeping the interior visible. This "one-sided-transparency" technique renders a more complete view of the tube's interior. When applied to virtual colonoscopy (VC), it compares favorably to existing methods. It provides more complete images, reduces computational time, and reduces memory requirements while preserving VCs benefits for patients and practitioners. The approach also has various potential uses outside of VC.

BACKGROUND OF THE INVENTION

Visualization of tubular objects is important for many applications, such as virtual colonoscopy (VC). Volume data is often rendered as a surface, as it is a good way to visualize complex objects. In order to visualize a solid object as a surface, it is necessary to first convert the input data into a mesh representation. In 1999, Bernardini et al. described one such approach for representation of 3D data using triangular mesh. In most cases, the objective is to visualize the exterior surface of the triangle mesh. However, in applications such as VC, it is more beneficial to visualize the interior surface.

In a virtual colonoscopy the patient undergoes a Computed Tomography (CT) scan, and the data collected, slices of 2D images, from the scan are used to create a 3D representation of the colon. VC aims to quantify the internal texture of the colon. Common VC visualization techniques include virtual fly-through (FT) such as taught in U.S. Pat. No. 6,331,116 and virtual fly-over (FO) such as taught in U.S. Published Application 2008/0069419, both incorporated herein by reference. Both techniques simulate a real colonoscopy by moving a virtual camera with a specific field of view along a planned path inside the colon, rendering internal views. Navigation can move from either the colon rectum (antegrade) or its cecum (retrograde).

Both FT and FO use the centerline as their navigation path; as the centerline is the locus of points distant from the colon boundary and provides complete visualization without blind areas. However, up to 20% of colonic mucosa is missed by a unidirectional fly-through, and about 8% are missed in fly-over, especially in the cases of poorly distended colon surfaces.

Thus, thorough/detailed VC examination, using FT, requires supine and prone antegrade and retrograde fly-throughs: a total of four fly-through operations, which is time consuming for medical staff. Fly-over does not suffer such limitations, yet it is computationally more complicated and requires two virtual cameras instead of one.

Other visualization techniques known in the art are not dependent on the centerline for navigation, but likewise require a planned path. Their visibility coverage exceeds that of traditional centerline-based fly-throughs. Still, polyps hidden between narrow haustral folds can be overlooked, and the resulting colon representation distorts the lumen, which distorts polyps and affects their visibility.

In 2006, a fly-over (FO) visualization technique was proposed by Hassouna eta/that overcame the limitations of existing approaches (especially fly-through and flattening). Splitting the entire colon into two halves, it gave each half a virtual camera for fly-over navigation. This technique covered up to 20% more than fly-through navigation. Additionally, only two traversals of the colon were required as compared to the four transversals for fly-throughs. However, splitting the colon requires much computation, and polyps located exactly at the split can potentially be missed. Splitting the colon could also result in ambiguities of the visualization of the colon surface, as the colon's toplogy may lead to allocating incorrect regions of the lumen at a particular visualization instance, if such regions are closer to the centerline than the correct location, leading to "holes" in the colon surface.

Thus, a method is needed that will provide more complete images, reduce computational time, and reduce memory requirements compared to technology of the prior art, while preserving VCs benefits for patients and practitioners.

SUMMARY OF THE PRESENT INVENTION

The present development is a virtual visualization technique that employs a one-sided transparency (OST) technique. The OST method both simplifies the VC computation and improves on the existing fly-over methods. The outcome, when OST is combined with fly-over, is a robust and computationally-efficient visualization.

DESCRIPTION OF THE FIGURES

FIG. 5 is a comparison of a boundary polyp using original fly-over and OST fly-over; and, FIG. 6 is a comparison of a boundary polyp using OST fly-over and fly-through.

DETAILED DESCRIPTION OF THE PRESENT DEVELOPMENT

The present invention is a method for tubular object visualization that renders the exterior of the tube essentially invisible while keeping the interior visible. The technique is referred to herein as "one-sided-transparency" or OST. When applied to virtual colonoscopy (VC), the method provides more complete images, reduces computational time, and reduces memory requirements compared to the prior art methods while preserving VC benefits for patients and practitioners. While demonstrated on virtual colonoscopy, this method is expected to have potential uses beyond VC.

Figure 1:
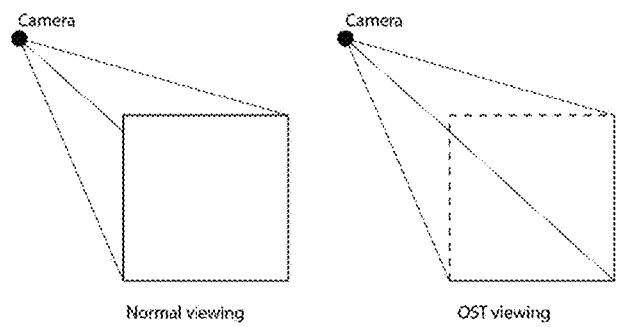
FIG. 1 is a comparison of normal view and one-sided transparency (OST)

One-sided transparency (OST) is an approach that visualizes tubular object shapes by making the interior surface opaque while the external surface is transparent. FIG. 1 illustrates typical or normal viewing from VC as compared to a view using the OST method of the present invention.

OST integrates back-face culling in order to make the outside face essentially invisible allowing the interior face to become visible. This is a three-step process: (1) a model is created such that the normal for each face of the model points towards the inside of the model; (2) back-face culling is applied to the model using techniques known in the art; (3) the model is viewed from the outside. When the model is viewed from the outside, the faces whose normals point away from the camera are culled, leaving only faces whose normal point toward the camera.

Figure 2:
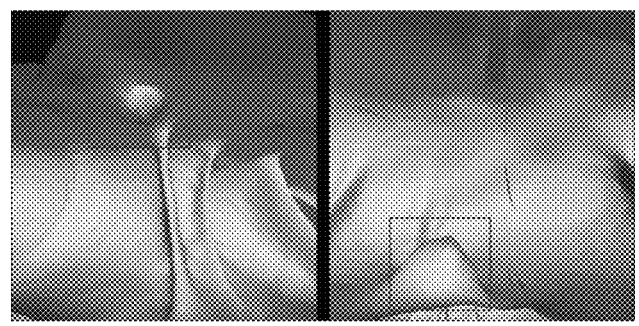
FIG. 2 is an image of a polyp near a camera at different rotations.
Figure 2:
Figure 2:

FIG. 2 is an image of a polyp, or a spherical object, near a camera at different rotations, such as might be produced using a tomographic slice of a colon; VC visibility starts at the point where the line from the camera to the colon is tangent. At a distance d=r, 240° of the colon are visible. Each VC camera thus covers two-thirds of the entire colon, meaning that the two cameras used in the splitting fly-over deliver overlapping visibility. Then it becomes clear that there will always be overlap no matter the distance between the camera and subject is.

Figure 3:
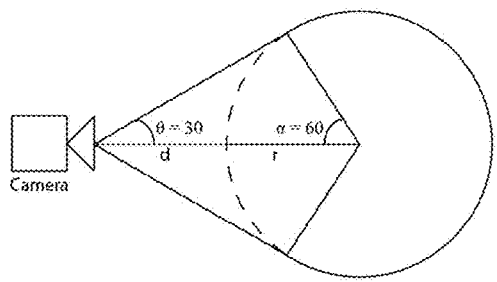
FIG. 3 demonstrates the visibility using OST.

As shown in FIG. 3, OST resolves the issue of possibly overlooking polyps on the boundary because no boundary issue exists with OST. This is because a polyp is not transparent until its edges become aligned with a camera, and this occurs only when the polyp is well within view of the opposing camera. Therefore two cameras provide a sufficient visualization. The prior art proposes using the splitting fly-over while making multiple VC cuts, thus catching the boundary polyps in other views. However, this can be too costly computationally.

Camera orientation is crucial to any fly-over method. The camera must be located perpendicular to the centerline in order to create the fly-over view. During movement the views must remain consistent. A camera that spins wildly around the centerline or shakes erratically is of little use.

In order to locate the camera perpendicular to the centerline, in the present method the normal at each point of the centerline is calculated. The first normal is determined by finding the vector between the first two points $p_1$ and $p_2$:

$$v_{\Delta 1} = p_2 - p_1$$

If this vector is not along the Z axis, then an arbitrary normal can be determined by the equation:

$$v_{N_1}(x,y,z) = (v_{\Delta 1}(y), -v_{\Delta 1}(x), 0)$$

If it is along the Z axis, then there is a normal is determined by:

$$v_{N_1}(x,y,z) = (1,0,0)$$

The first fly-over point is then:

$$p_{FO_1} = p_1 + v_{N_1}$$

The present method uses two cameras and the second camera is positioned at the reverse fly-over point $$p_{FO_1} = p_1 + v_{N_1}$$

located directly opposite $p_{FO_1}$ with respect to $p_1$:

$$p_{FO_{1R}} = p_1 - v_{N_1}$$

Figure 4:
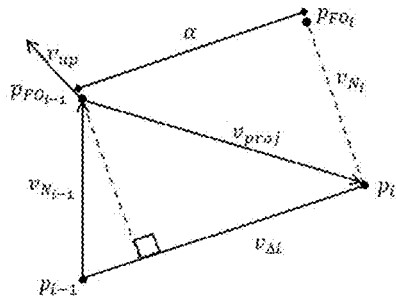
FIG. 4 shows the normal and the view up vectors for calculations.

In order to maintain continuity between camera views while moving, the present method relates each normal to the previous normal. The method for determining each normal vector is shown in FIG. 4. First, find the $\hat{v}_{\Delta i}$, the previous unit normal vector, and $v_{proj}$, the vector from the previous fly-over point $p_{FO_{i-1}}$ to the current point $p_i$:

$$v_{\Delta i} = p_i - p_{i-1}$$

$$\hat{v}_{\Delta i} = \frac{v_{\Delta i}}{|v_{\Delta i}|}$$

$$v_{proj} = p_i - p_{FO_{i-1}}$$

Then project $v_{proj}$ onto $\hat{v}_{\Delta i}$ to determine $\alpha$, which is the distance needed to move the previous fly-over point:

$$\alpha = v_{\Delta i} \cdot v_{N_{i-1}}$$

Next, use this distance to find the new fly-over point $p_{FO_i}$ by offsetting the previous fly-over point $p_{FO_i}$:

$$p_{FO_i} = p_{FO_{i-1}} + \alpha \hat{v}_{\Delta i}$$

With this new fly-over point it is now possible to find the new normal as well as the reverse fly-over point:

$$v_{N_i} = p_{FO_i} - o_i$$

$$p_{FO_{iR}} = p_i - v_{N_i}$$

Based on these calculations, the camera position is set at $p_{FO_i}$ and its focus is $p_i$.

Finally, a view up vector for the camera must be chosen that will maintain a consistent rotation. To align the vector to the centerline, a vector that is normal to the centerline is chosen. The view up vector for point $p_{i-1}$ is shown as $v_{up}$ in FIG. 4. The vector permits the camera to rotate easily in a perfect circle around the centerline. It also keeps a consistent left-to-right traversal of the colon, providing a stable frame of reference for the viewer. The view up vector $v_{up}$ for point $p_i$ is determined by:

$$v_{\Delta i+1} = p_{i+1} - p_i$$

$$v_{up} = v_{N_i} \times v_{\Delta i+1}$$

In an exemplary embodiment, not intended to be limiting with respect to scope of the development, the algorithm was tested using navigation techniques applied on 7 Computed Tomography (CT) colonography sets. One set was provided by the 3DR Inc., Louisville, Ky., and the rest were received from the Virtual Colonoscopy Center, Walter Reed Army Medical Center, Washington, D.C. The patients underwent standard 24-hour colonic preparation by oral administration of 90 ml of sodium phosphate and 10 mg of bisacodyl; then consumed 500 ml of barium for solid-stool tagging and 120 ml of Gastrografin to opacify luminal fluid. The CT protocol included 1.25 to 2.5 mm collimation, and 100 mAs and 120 kVp scanner settings. Each dataset contains 400~500 slices, and the spatial resolution for is 1.0×1.0×1.0 mm³. Synthetic polyps were created that were expected to be difficult to locate and the OST fly-over method was used to locate them.

Figure 5:
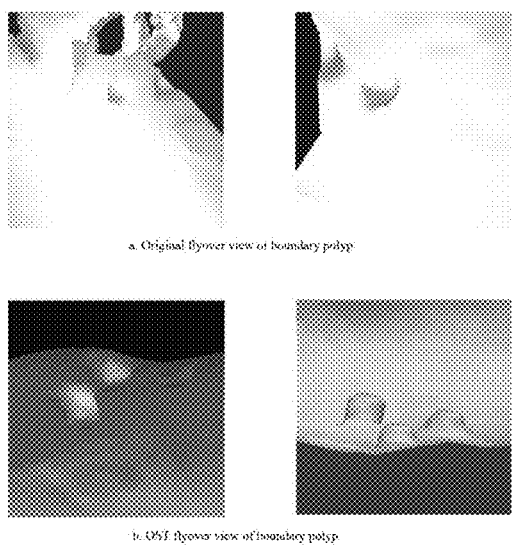
Figure 6:
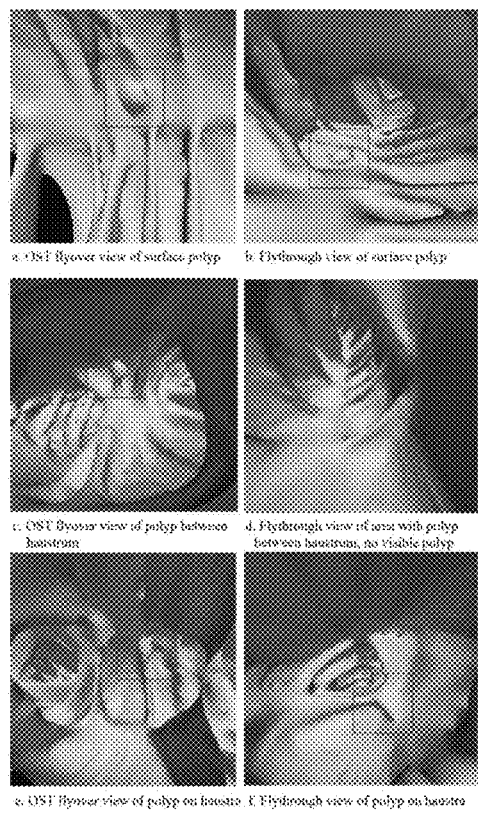

FIG. 5 highlights how the boundary issue of the original fly-over method is resolved using the OST fly-over method. With the original method, polyps on the boundary would be cut off and may not be recognizable as a polyp as seen in FIG. 5(a). The OST fly-over method results in FIG. 5(b), showing not only the polyp straddling the boundary but also the third polyp just on the other side of it. FIG. 5(a,b) show a surface polyp detectable using both methods. FIG. 5(c) shows a polyp between haustrum that was not visible using fly-through because it was blocked by the folds. In FIG. 5(d), the polyp is behind the fold at the top of the image. FIG. 5(e,f) show a polyp on a haustra. Although the polyp is visible using fly-through, it is not apparent that it is a polyp. The original fly-over program took ~5 minutes to start, the OST fly-over took ~20 seconds.

As compared to the prior art, the OST method of the present development vastly simplifies and optimizes the splitting fly-over method, obviating almost all of the extensive initial computation and risk of data loss at the cutpoint. Specifically, OST fly-over method is better than previous fly-over methods in terms of computational speed, coverage, and memory usage. Thus the physician can pull up the visualization significantly faster.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

It is understood that, in light of a reading of the foregoing description and drawings, those with ordinary skill in the art will be able to make changes and modifications to the present invention without departing from the spirit or scope of the invention, as defined herein.

What is claimed is:

1. A method for generating a three-dimensional image of a tubular object having an exterior surface and an interior surface and defining a centerline using a virtual visualization technique, the method comprising:
   a. providing a first virtual camera at a predetermined coordinate site perpendicular to the centerline of the object wherein the first virtual camera is directed toward the interior surface of the object;
   b. providing a second virtual camera at a predetermined coordinate site perpendicular to the centerline of the object and directly opposite the first virtual camera relative to the centerline wherein the second virtual camera is directed toward the interior surface of the tubular object;
   c. defining the tubular object by a set of points wherein each point defines a normal vector pointing toward the interior face of the object;
   d. having the first virtual camera capture the location of a point that has a normal vector pointed directly at the first virtual camera, and having the second virtual camera capture the location of a point that has a normal vector pointed directly at the second virtual camera and defining the captured point locations as data point capture data;
   e. moving the first virtual camera and the second virtual camera simultaneously along the length of the object while maintaining the relative relationship of the first virtual camera to the second virtual camera;
   f. repeating steps (d) and (e) for the entire circumference and length of the object;
   g. translating the data point capture data into a plurality of images; and,
   h. consolidating the plurality of images to define a three dimensional image wherein the exterior surface of the tubular object is rendered transparent while the interior surface of the tubular object is rendered opaque.

2. The method of claim 1 wherein the first virtual camera is positioned by calculating the normal vector by finding a vector $v_{N_1}$ between two points $p_1$ and $p_2$ on the centerline and then positioning the first virtual camera at a first fly-over point based on the normal vector as determined by the calculation $p_{FO_1} = p_1 + v_{N_1}$ and wherein the second virtual camera is positioned at a reverse fly-over point $$p_{FO_{1R}}$$

located directly opposite $p_{FO_1}$ with respect to $p_1$.

3. The method of claim 1 wherein continuity is maintained between camera views while moving the virtual cameras in step (e) by relating each normal to the previous normal.

4. The method of claim 1, wherein said step of capturing the location of the point comprises applying back-culling.

* * * * *